United States Patent
Bechtel et al.

(10) Patent No.: US 11,478,170 B2
(45) Date of Patent: Oct. 25, 2022

(54) OXIMETER PROBE WITH LIGHT WAVELENGTHS TO AVOID SURGICAL DYES

(71) Applicant: ViOptix, Inc., Newark, CA (US)

(72) Inventors: Kate Leeann Bechtel, Pleasant Hill, CA (US); Lester John Lloyd, Orinda, CA (US)

(73) Assignee: ViOptix, Inc., Newark, CA (US)

( * ) Notice: Subject to any disclaimer, the term of this patent is extended or adjusted under 35 U.S.C. 154(b) by 410 days.

(21) Appl. No.: 16/461,000

(22) Filed: Jul. 2, 2019

(65) Prior Publication Data

US 2019/0320958 A1    Oct. 24, 2019

Related U.S. Application Data

(60) Division of application No. 14/977,578, filed on Dec. 21, 2015, now Pat. No. 10,335,069, which is a (Continued)

(51) Int. Cl.
*A61B 5/1455* (2006.01)
*A61B 90/00* (2016.01)
(Continued)

(52) U.S. Cl.
CPC ........ *A61B 5/14551* (2013.01); *A61B 5/0059* (2013.01); *A61B 5/0075* (2013.01);
(Continued)

(58) Field of Classification Search
CPC .............. A61B 5/14551; A61B 5/1455; A61B 5/14552; A61B 5/7282; A61B 5/7246; A61B 5/7405; A61B 5/742
See application file for complete search history.

(56) References Cited

U.S. PATENT DOCUMENTS

| 4,223,680 A | 9/1980 | Jobsis |
| 4,286,599 A | 9/1981 | Hahn et al. |

(Continued)

FOREIGN PATENT DOCUMENTS

| JP | 5261088 | 10/1993 |
| JP | 10216115 A | 8/1998 |

(Continued)

OTHER PUBLICATIONS

Mittnacht, et al., "Methylene Blue Administration is Associated with Decreased Cerebral Oximetry Values," Anesthesia & Analgesia, Aug. 2008, vol. 105, No. 2, pp. 549-550.

(Continued)

*Primary Examiner* — Marjan Fardanesh
(74) *Attorney, Agent, or Firm* — Aka Chan LLP

(57) ABSTRACT

A tissue oximetry device utilizes at least three or at least four different wavelengths of light for collection of reflectance data where the different wavelengths are longer than 730 nanometers. The three or four wavelengths are utilized to generate a range of reflectance data suited for accurate determination of oxygenated hemoglobin and deoxygenated hemoglobin concentrations. The relatively long wavelengths decrease optical interference from certain dyes, particularly methylene blue and PVPI, which may be present on tissue being analyzed for viability and further enhance the generation of accurate reflectance data. The wavelengths are 760 nanometers, 810 nanometers, and 850 nanometers, or 760 nanometers, 810 nanometers, 850 nanometers, and 900 nanometers.

21 Claims, 5 Drawing Sheets

Related U.S. Application Data continuation of application No. 13/887,178, filed on May 3, 2013, now Pat. No. 9,216,000.

(60) Provisional application No. 61/682,146, filed on Aug. 10, 2012, provisional application No. 61/642,393, filed on May 3, 2012, provisional application No. 61/642,389, filed on May 3, 2012, provisional application No. 61/642,395, filed on May 3, 2012, provisional application No. 61/642,399, filed on May 3, 2012.

(51) Int. Cl.
| | | |
|---|---|---|
| *A61B 5/00* | (2006.01) | |
| *A61B 5/1495* | (2006.01) | |
| *A61M 35/00* | (2006.01) | |
| *A61B 5/145* | (2006.01) | |
| *A61B 90/11* | (2016.01) | |
| *A61B 5/1459* | (2006.01) | |
| *A61B 90/30* | (2016.01) | |

(52) U.S. Cl.
CPC .......... *A61B 5/1455* (2013.01); *A61B 5/1459* (2013.01); *A61B 5/1495* (2013.01); *A61B 5/14546* (2013.01); *A61B 5/14552* (2013.01); *A61B 5/72* (2013.01); *A61B 5/7246* (2013.01); *A61B 5/7282* (2013.01); *A61B 5/74* (2013.01); *A61B 5/742* (2013.01); *A61B 5/7405* (2013.01); *A61B 5/7475* (2013.01); *A61B 90/11* (2016.02); *A61B 90/39* (2016.02); *A61M 35/003* (2013.01); *A61B 2090/065* (2016.02); *A61B 2090/306* (2016.02); *A61B 2090/395* (2016.02); *A61B 2560/0431* (2013.01); *A61B 2560/0475* (2013.01); *A61B 2562/0271* (2013.01); *A61B 2562/166* (2013.01)

(56) References Cited

U.S. PATENT DOCUMENTS

| | | | |
|---|---|---|---|
| 5,088,493 | A | 2/1992 | Giannini et al. |
| 5,218,962 | A | 6/1993 | Mannheimer et al. |
| 5,517,301 | A | 5/1996 | Dave |
| 5,517,987 | A | 5/1996 | Tsuchiya |
| 5,690,113 | A | 11/1997 | Sliwa et al. |
| 6,056,692 | A | 5/2000 | Schwartz |
| 6,070,093 | A | 5/2000 | Oosta et al. |
| 6,078,833 | A | 6/2000 | Hueber |
| 6,197,034 | B1 | 3/2001 | Gvozdic et al. |
| 6,285,904 | B1 | 9/2001 | Weber et al. |
| 6,453,183 | B1 | 9/2002 | Walker |
| 6,516,209 | B2 | 2/2003 | Cheng et al. |
| 6,549,284 | B1 | 4/2003 | Boas et al. |
| 6,587,701 | B1 | 7/2003 | Stranc et al. |
| 6,587,703 | B2 | 7/2003 | Cheng et al. |
| 6,597,931 | B1 | 7/2003 | Cheng et al. |
| 6,708,048 | B1 | 3/2004 | Chance |
| 6,735,458 | B2 | 5/2004 | Cheng et al. |
| 6,766,188 | B2 | 7/2004 | Soller |
| 6,839,580 | B2 | 1/2005 | Zonios et al. |
| 7,247,142 | B1 | 7/2007 | Elmandjra et al. |
| 7,254,427 | B2 | 8/2007 | Cho et al. |
| 7,344,587 | B2 | 3/2008 | Kahn et al. |
| D567,949 | S | 4/2008 | Lash et al. |
| 7,355,688 | B2 | 4/2008 | Lash et al. |
| D568,479 | S | 5/2008 | Mao et al. |
| 7,657,293 | B2 | 2/2010 | Lash et al. |
| 8,798,700 | B1 | 8/2014 | Heaton et al. |
| 2002/0019587 | A1 | 2/2002 | Cheng et al. |
| 2002/0179094 | A1 | 12/2002 | Perlow |
| 2004/0111016 | A1 | 6/2004 | Casscells et al. |
| 2004/0260161 | A1 | 12/2004 | Melker |
| 2005/0177069 | A1 | 8/2005 | Takizawa et al. |
| 2005/0250998 | A1 | 11/2005 | Huiku |
| 2005/0277818 | A1 | 12/2005 | Myers |
| 2006/0129037 | A1 | 6/2006 | Kaufman et al. |
| 2007/0149886 | A1 | 6/2007 | Kohls |
| 2008/0015422 | A1 | 1/2008 | Wessel |
| 2008/0015424 | A1 | 1/2008 | Bemreuter |
| 2008/0139908 | A1 | 6/2008 | Kurth |
| 2008/0181715 | A1 | 7/2008 | Cohen |
| 2008/0319290 | A1 | 12/2008 | Mao et al. |
| 2009/0234209 | A1 | 9/2009 | Lash et al. |
| 2009/0275805 | A1 | 11/2009 | Lane et al. |
| 2010/0010486 | A1 | 1/2010 | Mehta et al. |
| 2011/0028814 | A1 | 2/2011 | Petersen et al. |
| 2011/0046458 | A1 | 2/2011 | Pinedo et al. |
| 2011/0205535 | A1 | 8/2011 | Soller et al. |
| 2011/0224518 | A1 | 9/2011 | Tindi et al. |
| 2011/0237911 | A1 | 9/2011 | Lamego et al. |

FOREIGN PATENT DOCUMENTS

| | | |
|---|---|---|
| JP | 11244268 A | 12/1999 |
| JP | 2006109964 | 4/2006 |
| KR | 1020000075056 | 12/2000 |
| KR | 1020090016744 | 2/2009 |
| WO | 2011008382 | 1/2011 |

OTHER PUBLICATIONS

Alexandrakis, et al., "Accuracy of the Diffusion Approximation in Determining the Optical Properties of a Two-Layer Turbid Medium," Applied Optics, vol. 37, No. 31, Nov. 1, 1998, pp. 7403-7409.

Hueber, Dennis et al., "New Optical Probe Designs for Absolute (Self-Calibrating) NIR Tissue Hemoglobin Measurements," in Proceedings of Optical Tomography and Spectroscopy of Tissue III, vol. 3597, 618-631(Jan. 1999).

Tseng, et al., "Analysis of a Diffusion-Model-Based Approach for Efficient Quantification of Superficial Tissue Properties," Optics Letters, vol. 35, No. 22, Nov. 15, 2010, pp. 3739-3741.

Tseng, et al., "In Vivo Determination of Skin Near-Infrared Optical Properties Using Diffuse Optical Spectroscopy," Journal of Biomedical Optics, vol. 13(1), 014016, Jan./Feb. 2008, pp. 1-7.

Seo, et al., "Perturbation and Differential Monte Carlo Methods for Measurement of Optical Properties in a Layered Epithelial Tissue Model," Journal of Biomedical Optics, vol. 12(1), 014030, Jan./Feb. 2007, pp. 1-15.

Nichols, et al., "Design and Testing of a White-Light, Steady-State Diffuse Reflectance Spectrometer for Determination of Optical Properties of Highly Scattering Systems," Applied Optics, vol. 36, No. 1, Jan. 1, 1997, pp. 93-104.

Kienle, et al., "Spatially Resolved Absolute Diffuse Reflectance Measurements for Noninvasive Determination of the Optical Scattering and Absorption Coefficients of Biological Tissue," Applied Optics, vol. 35, No. 13, May 1, 1996, pp. 2304-2314.

Fawzi, et al., "Determination of the Optical Properties of a Two-Layer Tissue Model by Detecting Photons Migrating at Progressively Increasing Depths," Applied Optics, vol. 42, No. 31, Nov. 1, 2003, pp. 6398-6411.

Farrell, et al., "Influence of Layered Tissue Architecture on Estimates of Tissue Optical Properties Obtained from Spatially Resolved Diffuse Reflectometry," Applied Optics, vol. 37, No. 10, Apr. 1, 1998, pp. 1958-1972.

Dam, et al., "Determination of Tissue Optical Properties from Diffuse Reflectance Profiles by Multivariate Calibration," Applied Optics, vol. 37, No. 4, Feb. 1, 1998, pp. 772-778.

Cen, et al., "Optimization of Inverse Algorithm for Estimating the Optical Properties of Biological Materials Using Spatially-Resolved Diffuse Reflectance," Inverse Problems in Science and Engineering, vol. 18, No. 6, Sep. 2010, pp. 853-872.

OXIMETER PROBE WITH LIGHT WAVELENGTHS TO AVOID SURGICAL DYES

CROSS-REFERENCE TO RELATED APPLICATIONS

This patent application is a divisional of U.S. patent application Ser. No. 14/977,578, filed Dec. 21, 2015, issued as U.S. Pat. No. 10,335,069 on Jul. 2, 2019, which is a continuation of U.S. patent application Ser. No. 13/887,178, filed May 3, 2013, issued as U.S. Pat. No. 9,216,000 on Dec. 22, 2015, which claims the benefit of U.S. patent applications 61/642,389, 61/642,393, 61/642,395, and 61/642,399, filed May 3, 2012, and 61/682,146, filed Aug. 10, 2012. These applications are incorporated by reference along with all other references cited in this application.

BACKGROUND OF THE INVENTION

The present invention relates generally to optical systems that monitor oxygen levels in tissue. More specifically, the present invention relates to optical probes that include sources and detectors on sensor heads of the optical probes for emitting and detecting light.

Oximeters are medical devices used to measure oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or personal training for a marathon); and veterinary purposes (e.g., animal monitoring).

Pulse oximeters and tissue oximeters are two types of oximeters that operate on different principles. A pulse oximeter requires a pulse in order to function. A pulse oximeter typically measures the absorbance of light due to the pulsing arterial blood. In contrast, a tissue oximeter does not require a pulse in order to function, and can be used to make oxygen saturation measurements of a tissue flap that has been disconnected from a blood supply.

Human tissue, as an example, includes a variety of molecules that can interact with light via scattering or absorption (e.g., via light-absorbing chromophores). Such chromophores include oxygenated and deoxygenated hemoglobins, melanin, water, lipid, and cytochrome. Oxygenated and deoxygenated hemoglobins are the most dominant chromophores in the spectrum range of 600 nanometers to 900 nanometers. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving measurement accuracy; reducing measurement time; lowering cost; reducing size, weight, or form factor; reducing power consumption; and for other reasons, and any combination of these.

In particular, assessing a patient's oxygenation state is important as it is an indicator of the state of the patient's health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of nonideal conditions. While existing oximeters have been sufficient for post-operative tissue monitoring where speed of measurement is less critical, existing oximeters fluctuate substantially and give inaccurate saturation measurements when used during surgery where various elements can interfere with accurate reading, such as if the oximeter comes in contact with blood.

Therefore, there is a need for improved tissue oximetry probes and methods of making measurements using these probes.

BRIEF SUMMARY OF THE INVENTION

A tissue oximetry device utilizes at least two different wavelengths of light for collection of reflectance data where the wavelengths are above 700 nanometers. Utilizing two, three, or four wavelengths generates a range of data that is suited for accurate determination of oxygenated hemoglobin and deoxygenated hemoglobin concentrations.

According to one embodiment, a tissue oximetry device includes a processor; a memory coupled to the processor; and a plurality of light sources. The light sources are controlled by the processor, and generate and emit at least two wavelengths of light longer than 700 nanometers. The tissue oximetry device further includes a plurality of detectors configured to be controlled by the processor. The processor is configured to: control the plurality of light sources to generate and emit the light into tissue, control the plurality of detectors to detect the light subsequent to reflection of the light from the tissue, control the plurality of detectors to generate reflectance data for the tissue based on detection of the light by the plurality of detectors, and determine the oxygen saturation for the tissue based on the reflectance data.

According to one specific embodiment, the at least two wavelengths are approximately 760 nanometers and 850 nanometers. According to an alternative specific embodiment, the plurality of light sources is configured to generate and emit at least three wavelengths of light having wavelengths of 760 nanometers, 810 nanometers, and 850 nanometers. According to another alternative specific embodiment, the plurality of light sources is configured to generate and emit at least four wavelengths of light having wavelengths of approximately 760 nanometers, 810 nanometers, 850 nanometers, and 900 nanometers.

According to another embodiment, a tissue oximetry device includes a processor; a memory coupled to the processor; and a plurality of light sources that are controlled by the processor. The light sources are configured to generate and emit at least two wavelengths of light that are longer than wavelengths of primary absorption peaks of methylene blue. The tissue oximetry device further includes a plurality of detectors configured to be controlled by the processor. The processor is configured to: control the plurality of light sources to generate and emit the light into tissue; control the plurality of detectors to detect the light subsequent to reflection of the light from the tissue; control the plurality of detectors to generate reflectance data for the tissue based on detection of the light by the plurality of detectors; and determine the oxygen saturation for the tissue based on the reflectance data.

These relatively long wavelengths tend to decrease optical interference with certain dyes, particularly methylene blue and povidone-iodine (PVPI, e.g., Betadine® of Purdue Products L.P. of Stamford, Conn.), which may be present in tissue being analyzed for viability, and further enhances the generation of accurate reflectance data. The wavelengths also avoid gentian violet, which is often used in tissue marking pens. The wavelengths utilized by the tissue oximetry device are outside of the peak absorptive ranges of methylene blue, gentian violet, and PVPI. Therefore, relatively accurate reflectance data may be acquired in an increased number of surgical situations than was acquired by tissue oximetry device utilizing other wavelengths. Further, the use of these particular two, three, or four different wavelengths provides sufficient reflectance data to solve the two-variable, three-variable, or four-variable relations from which oxygenated hemoglobin and deoxygenated hemoglobin concentrations can be determined, depending on how many additional tissue chromophores are included (e.g., melanin, or others). The utilization of optimal probing wavelengths improves tissue oximetry device performance in intraoperative situations involving dyes as compared to the tissue oximetry devices considered to be prior art.

Other objects, features, and advantages of the present invention will become apparent upon consideration of the following detailed description and the accompanying drawings, in which like reference designations represent like features throughout the figures.

DETAILED DESCRIPTION OF THE INVENTION

Colored dyes often are present on or have been absorbed by the tissue regions that clinicians wish to check for viability. Methylene blue is one dye that is often used for sentinel lymph node biopsies, which are often performed during the same surgical session as a mastectomy in order to determine the degree to which cancerous tissue may have spread. Therefore, methylene blue can be present in the tissue being analyzed for viability for reconstruction or the like. Methylene blue absorbs light readily in the 500 nanometer to 700 nanometer range with the absorption tailing off at about 730 nm.

Povidone-iodine (PVPI, e.g., Betadine® of Purdue Products L.P. of Stamford, Conn.) is an orange dye that is often used as an antiseptic prior to making surgical incisions and may therefore also be present on tissue of interest. Similar to methylene blue, PVPI absorbs light readily in the 500 nanometer to 700 nanometer range, however to a lesser degree than methylene blue. Further, gentian violet is a dye that is often used in tissue marking pens, such as the pens used by plastic surgeons and may therefore be present on tissue of interest.

Figure 1:
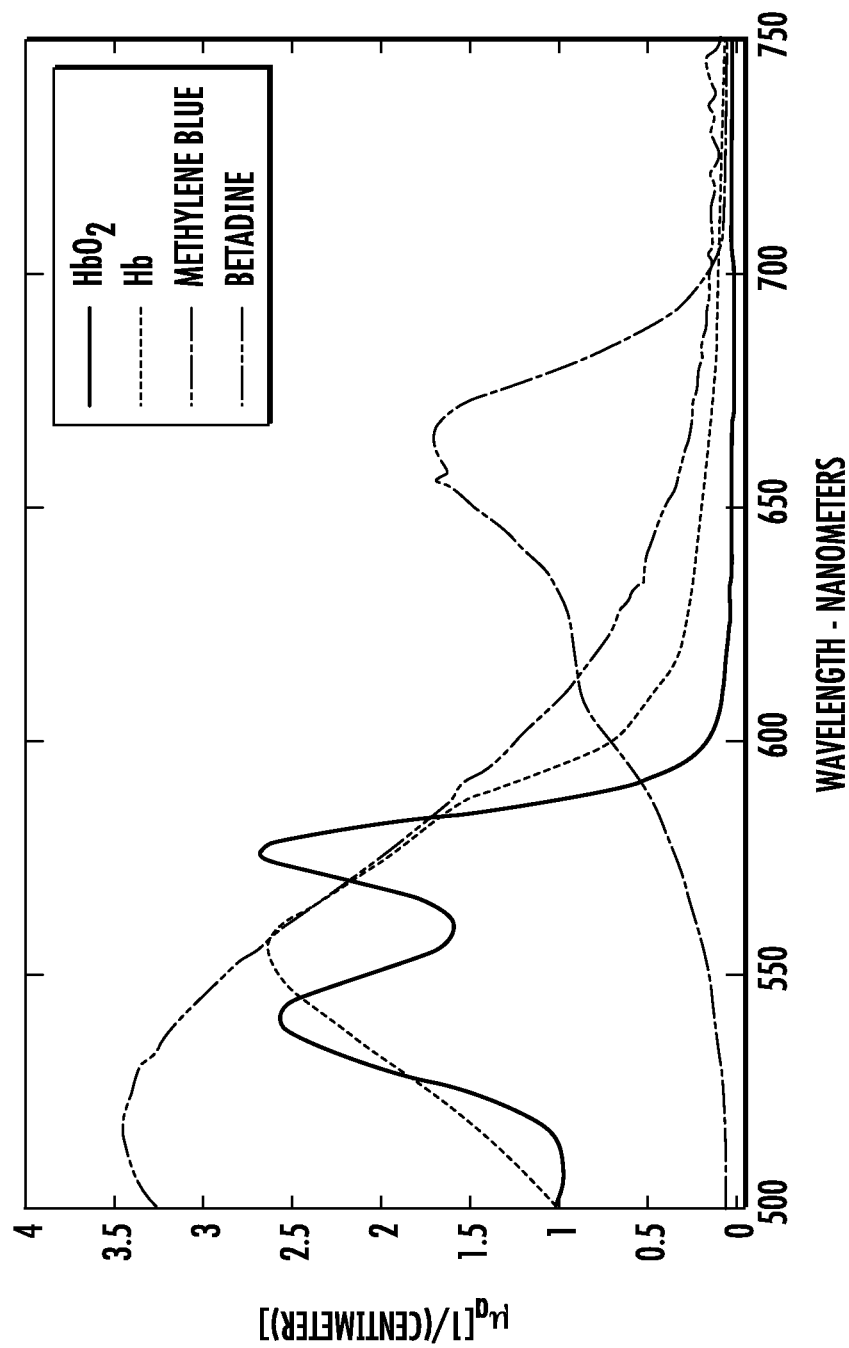
FIG. 1 is an absorption graph that shows the absorption coefficient of methylene blue and PVPI at wavelengths ranging from 500 nanometers to just below 750 nanometers and shows the predominant absorption of wavelengths below 700 nanometers for methylene blue.
Figure 2:
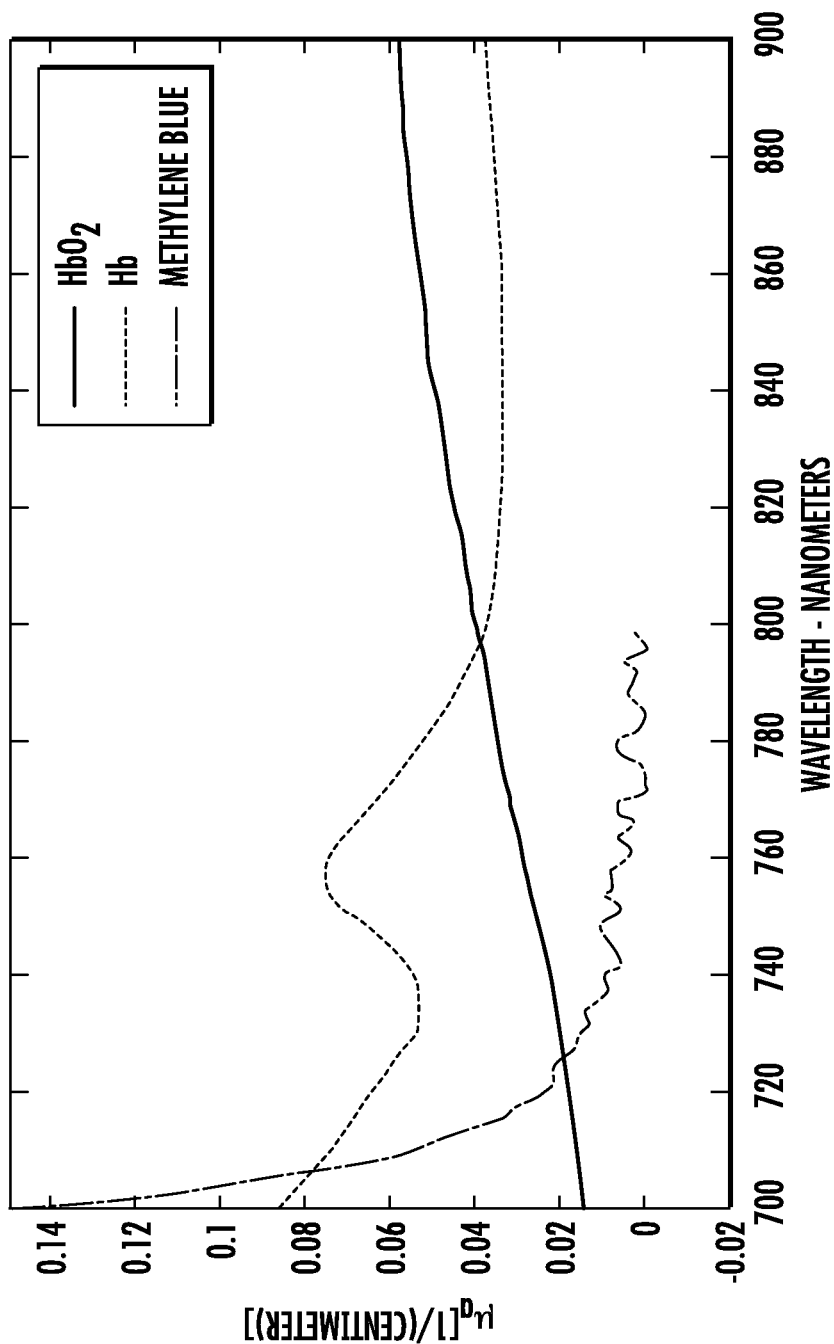
FIG. 2 is an absorption graph that shows the absorption coefficient of methylene blue at wavelengths ranging from 700 nanometers to 900 nanometers.

FIGS. 1 and 2 are absorption graphs that show the absorption coefficient $\mu a$ of methylene blue at wavelengths ranging from 500 nanometers to 900 nanometers. FIG. 1 also shows the predominant absorption by methylene blue of wavelengths below 700 nanometers and shows the primary absorption peaks of methylene blue centered at about 600 nanometers and 660 nanometers. FIG. 1 also shows the absorption coefficient $\mu a$ of PVPI at wavelengths ranging from 500 nanometers to just below 750 nanometers. FIG. 1 also shows the predominant absorption by PVPI of wavelengths below 650 nanometers and shows the primary absorption peak of PVPI centered at about 510 nanometers.

The presence of methylene blue, PVPI, or other dyes can interfere with the determinations of tissue viability. For example, surgeons may use tissue oximetry devices for determining the viability of tissue, and dyes present on the tissue can absorb the wavelengths used by the tissue oximetry devices for providing tissue viability information.

Figure 3:
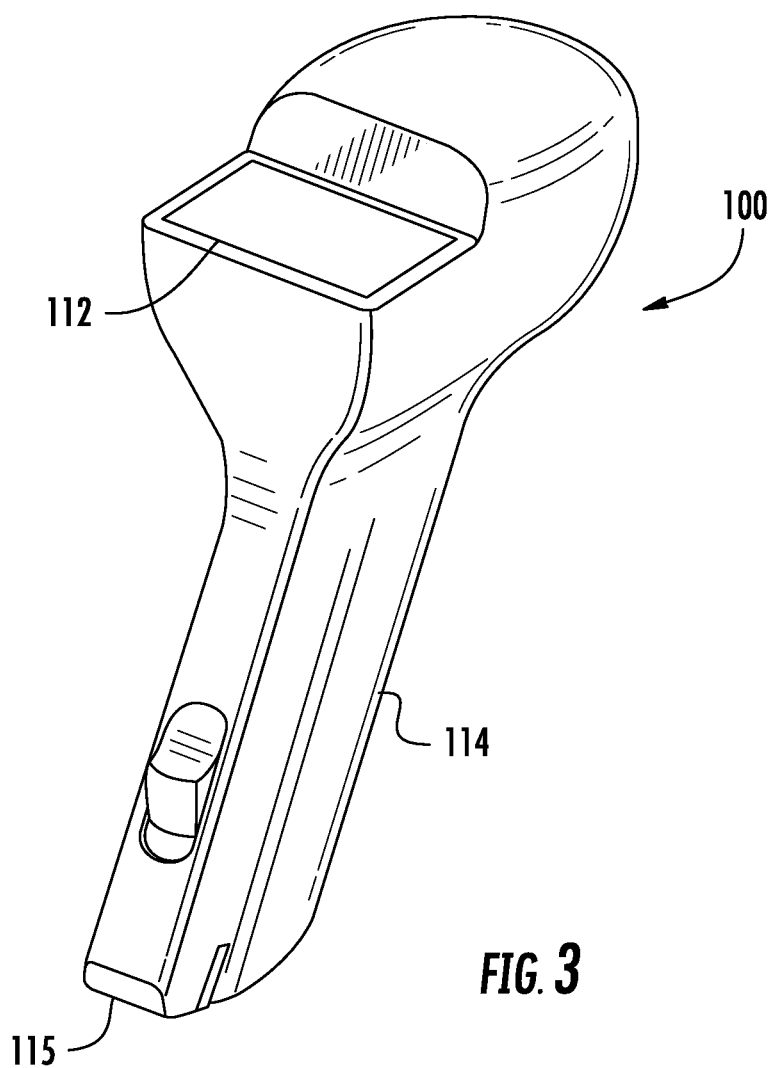
FIG. 3 is a simplified image of a tissue oximetry device according to one embodiment.

FIG. 3 is a simplified image of a tissue oximetry device 100 according to one embodiment. Tissue oximetry device 100 is configured to make tissue oximetry measurements, such as intraoperatively and postoperatively. In an implementation, the tissue oximetry device is handheld and can make tissue oximetry measurements and display these measurements, without needing to connect to another external component either via a cable or wirelessly. The electronics to make measurements and calculations is contained entirely within the housing of the tissue oximetry device. The tissue oximetry device is a standalone handheld tissue oximeter device, without a cable or wireless connection.

Tissue oximetry device 100 may be a handheld device that includes a tissue oximetry probe 115 (also sometimes referred to as a sensor head), which may be positioned at an end of a sensing arm 114. Tissue oximetry device 100 is configured to measure the oxygen saturation of tissue by emitting light, such as red and near-infrared light, from tissue oximetry probe 115 into tissue, and collecting light reflected from the tissue at the tissue oximetry probe.

Tissue oximetry device 100 may include a display 112 or other notification device that notifies a user of oxygen saturation measurements made by the tissue oximetry device. While tissue oximetry probe 115 is described as being configured for use with tissue oximetry device 100, which is a handheld device, tissue oximetry probe 115 may be used with other tissue oximetry devices, such as a modular tissue oximetry device where the tissue oximetry probe is at the end of a cable device that connects to a base unit. The cable device might be a disposable device that is configured for use with a single patient and the base unit might be a device that is configured for repeated use. Such modular tissue oximetry devices are well understood by those of skill in the art and are not described further.

Figure 4A:
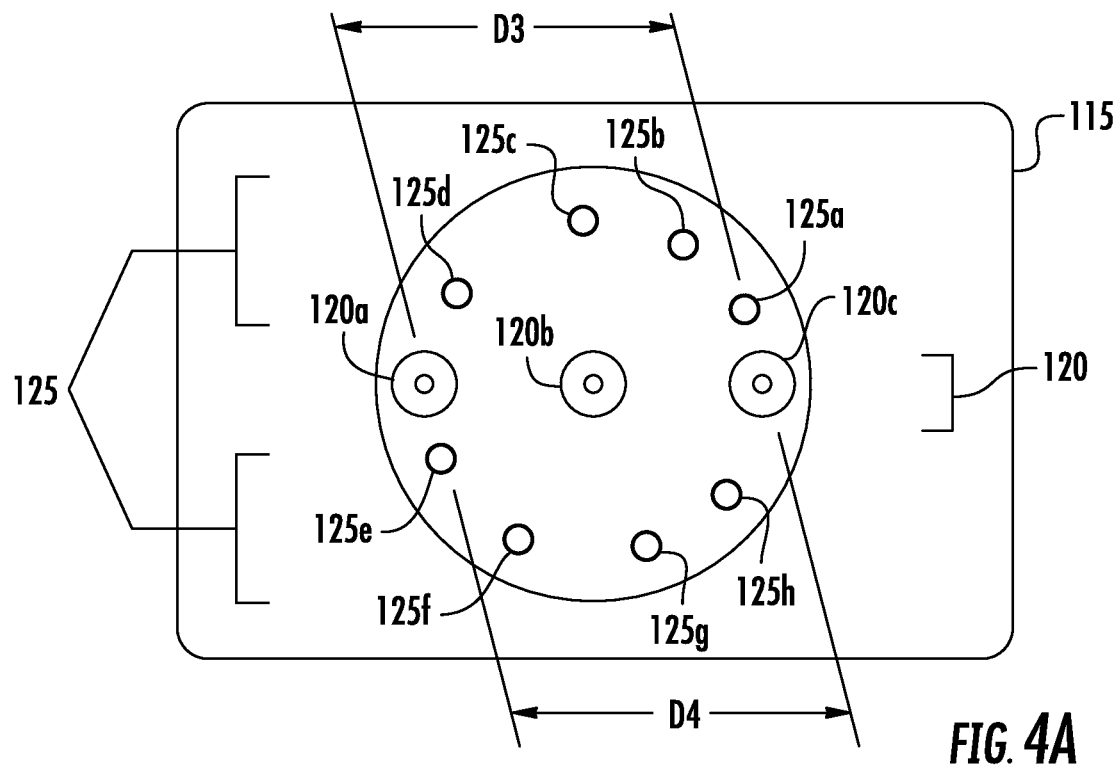
FIG. 4A is a simplified end view of the tissue oximetry probe according to one embodiment.
Figure 4B:
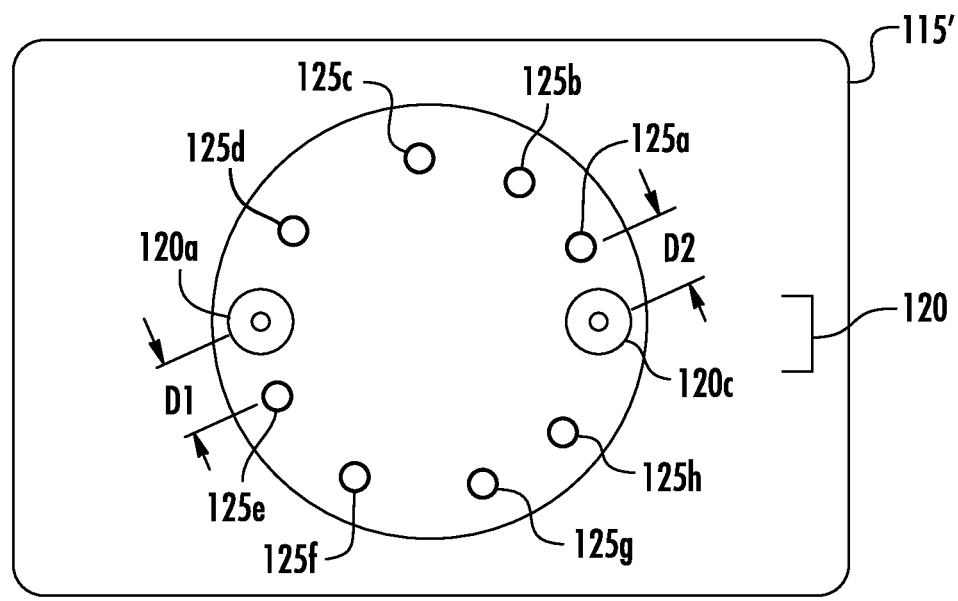
FIG. 4B is a simplified end view of the tissue oximetry probe according to an alternative embodiment.

FIG. 4A is a simplified end view of tissue oximetry probe 115 according to one embodiment. Tissue oximetry probe 115 is configured to contact tissue (e.g., a patient's skin) for which a tissue oximetry measurement is to be made. Tissue oximetry probe 115 includes a set of light sources 120 (generally light sources 120) and includes a set of detectors 125 (generally detectors 125). The set of light sources 120 may include two or more light sources. According to the embodiment shown in FIG. 4A, tissue oximetry probe 115 includes three light sources 120a, 120b, and 120c, but may alternatively include two light sources, such as light sources 120a and 120c where light source 120b is omitted. Additional light sources (not shown) can be added. FIG. 4B is a simplified end view of a tissue oximetry probe 115' according to an embodiment where the tissue oximetry probe includes the two light sources 120*a* and 120*c*, but does not include light source 120*b*. Aside from the different number of light sources, tissue oximetry probes 115 and 115' are substantially similar.

The set of detectors 125 may include eight detectors 125*a*, 125*b*, 125*c*, 125*d*, 125*e*, 125*f*, 125*g*, and 125*h* as shown, but may include more or fewer detectors. Detectors 125 are positioned with respect to outer light sources 120*a* and 120*c* such that eight or more (e.g., fourteen) unique source-to-detector distances are created. The shortest source-to-detector distances may be the same. For example, the shortest source-to-detector distance D1 between light source 120*a* and detector 125*e*, and the shortest source-to-detector distance D2 between light source 120*c* and detector 125*a* may be the same. It follows that the source-to-detector distance D3 between light source 120*a* and detector 125*a*, and the source-to-detector distance D4 between light source 120*c* and detector 125*e* may also be the same. The source-to-detector distances D3 and D4 are the longest source-to-detector distance for light sources 120*a* and 120*c*. With the exception of the shortest source-to-detector distance and the longest source-to-detector distance for light sources 120*a* and 120*c*, the source-to-detector distances for light sources 120*a* and 120*c* may be unique. As described above, tissue oximetry probe 115 may have fourteen unique source-to-detector distances that allow for fourteen reflectance data points to be collected by detectors 125 from each wavelength of light emitted from light sources 120. As described in further detail below, each light source 120 is configured to generate and emit a number of wavelengths.

Detectors 125 are solid state detectors and may be mounted on a printed circuit board (PCB, not shown), which routes various signal to and from the detectors. Further, detectors 125 may be combined devices or discrete devices.

While the tissue oximetry probes 115 and 115' are described above as having circularly arranged detectors, the detectors may be positioned in other arrangements, such as linear, triangular, rectangular, square, and others. In some embodiments, the light sources may also be alternatively arranged, such as in a triangular arrangement, a rectangular arrangement, and others.

In a specific implementation, detectors 125 are positioned with respect to outer light sources 120*a* and 120*c* such that four or more (e.g., fourteen) unique source-to-detector distances are created. With greater numbers of source-to-detector distances, this can be used to obtain greater accuracy, faster calibration, and redundancy (when duplicate source-to-detector distances are provided). At least two source-to-detectors distances are about 1.5 millimeters or less (e.g., 0.5 millimeters up to about 1.7 millimeters), and at least two more two source-to-detectors distances are about 2.5 millimeters or greater (e.g., 1.5 millimeters up to about 3.2 millimeters).

In other words, a first source-to-detector distance is about 1.5 millimeters or less. A second source-to-detector distance is about 1.5 millimeters or less. A third source-to-detector distance is about 2.5 millimeters or greater. A fourth source-to-detector distance is about 2.5 millimeters or greater. There can be various numbers of sources and detector arrangements to obtain these four source-to-detector distances, such as one source and four detectors, two sources and two detectors, one detector and four sources, or other arrangements and combinations.

For example, an implementation includes at least two sources and at least two detectors, where a maximum distance between a source and a detector is about 4 millimeters (or about 5 millimeters). At least two source-to-detector are about 2.5 millimeters or greater. At least two source-to-detector distances are about 1.5 millimeters or less.

When a greater number of sources and detectors are used, greater numbers of source-to-detector distances are available. As discussed, these can be used to provide greater accuracy, faster calibration, or redundancy, or a combination. The arrangement of the sources and detectors can be in circular pattern, such as at points along the arc of a circle with radius (e.g., 4 millimeters, or 5 millimeters). In an implementation, a tolerance of the detector or source positions on the arc is within 10 microns of the arc curve. In other implementations, the tolerance is within about 0.5 millimeters.

Wavelengths Generated and Emitted From the Light Sources

Each light source 120 may include a fiber optic cable and one or more light emitting diodes (LEDs) or laser diodes (generally wavelength sources) that transmit generated light into the fiber optic cable. For example, each light source 120 may include two or more wavelength sources that generate two or more substantially unique wavelengths. The wavelengths may all be longer than 730 nanometers, e.g., in the red and near infrared.

According to an embodiment where each light source 120 includes two wavelength sources, the wavelength sources may be configured to generate and emit wavelengths of approximately 760 nanometers (e.g., +/−10 nanometers), and 850 nanometers (e.g., +/−20 nanometers). According to an embodiment where each light source 120 includes three wavelength sources, the wavelength sources may be configured to generate and emit wavelengths of approximately 760 nanometers (e.g., +/−10 nanometers), 810 nanometers (e.g., +/−10 nanometers), and 850 nanometers (e.g., +/−20 nanometers). According to another embodiment, where each light source 120 includes four wavelength sources, the wavelength sources may be configured to emit wavelengths of approximately 760 nanometers (e.g., +/−10 nanometers), 810 nanometers (e.g., +/−10 nanometers), 850 nanometers (e.g., +/−20 nanometers), and 900 nanometers (e.g., +/−20 nanometers). Additional and/or alternative wavelengths may be utilized by tissue oximetry device 100.

Use of the described wavelengths by tissue oximetry device 100 tends to decrease the fraction of emitted light that can be absorbed by methylene blue, gentian violet, and PVPI, and thereby increases the fraction of light that can be scattered or absorbed by intrinsic tissue elements and generates accurate reflectance data. Accurate reflectance data is necessary in order to extract the optical properties of tissue from which the concentrations of oxygenated and deoxygenated hemoglobin can be derived.

For the foregoing described wavelengths, tissue scattering is relatively low and light penetrates farther into tissue than shorter wavelengths. Further, the foregoing described wavelengths are on both sides of an oxygenated-deoxygenated hemoglobin spectral crossing point called an isosbestic point, which is 810 nanometers for hemoglobin. As such, when one chromophore (e.g., oxygenated hemoglobin) has high absorption, the other chromophore (e.g., deoxygenated hemoglobin) then has low absorption and vice versa. The tissue oximetry device's utilization of wavelengths surrounding the isosbestic point provides for relatively improved statistics for oxygen saturation determinations.

In at least one of the foregoing described embodiments, tissue oximetry device 100 utilizes a wavelength at approximately the isosbestic point, at 810 nanometers. At the isosbestic point the absorption of the 810 nanometer wavelength for oxygenated hemoglobin and deoxygenated hemoglobin are equivalent and therefore provides a stable reference point in the reflectance data generated by detectors 125. Relatively longer wavelengths, such as the 900 nanometer wavelength of at least one embodiment allows for distinguishing between the absorption curve for deoxygenated hemoglobin from the absorption curve for melanin.

Tissue Oximetry Device Circuit

Figure 5:
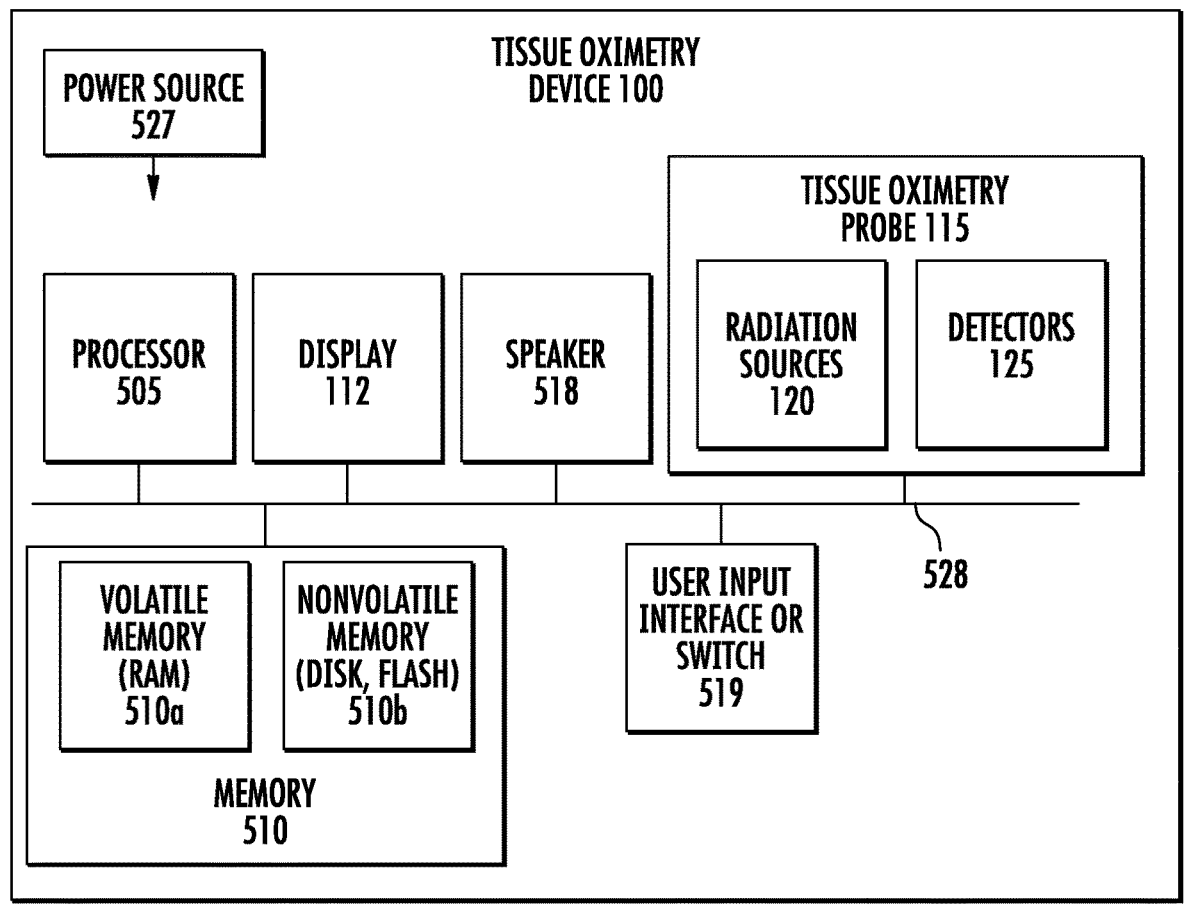
FIG. 5 is a block diagram of the tissue oximetry device according to one embodiment.

FIG. 5 is a block diagram of tissue oximetry device 100 according to one embodiment. Tissue oximetry device 100 according to the embodiment shown in FIG. 5 includes display 112, a processor 505, a memory 510, a speaker 518, one or more user-selection devices 519 (e.g., one or more switches for initiating oxygen saturation measurements), the set of light sources 120, the set of detectors 125, and a power source (e.g., a battery) 527. The foregoing listed components may be linked together via a bus 528, which may be the system bus architecture of tissue oximetry device 100. Although this figure shows one bus that connects to each component, the busing is illustrative of any interconnection scheme serving to link these components or other components included in tissue oximetry device 100 subsystems. For example, speaker 518 (e.g., an alternative device for notifying a user of oxygen saturation measurements) could be connected to a subsystem through a port or have an internal direct connection to processor 516. Further, the components described are housed in a mobile housing (see FIG. 1) of tissue oximetry device 100 according to at least one embodiment.

Processor 505 may include a microprocessor, a microcontroller, control logic, a multi-core processor, or the like. Further, processor 505 may control turning on and turning off the wavelength sources as described below. Memory 510 may include a variety of memories, such as a volatile memory 510a (e.g., a RAM), a nonvolatile memory 519b (e.g., a disk, Flash memory, electrically erasable memory, PROM, and others). Memory 510 may collect and store reflectance data generated by detectors 125. Different implementations of tissue oximetry device 100 may include any number of the listed components, in any combination or configuration, and may also include other components not shown.

Power source 127 can be a battery, such as a disposable battery. Disposable batteries are discarded after their stored charge is expended. Some disposable battery chemistry technologies include alkaline, zinc carbon, or silver oxide. The battery has sufficient stored charged to allow use of the handheld device for several hours. After use, the handheld unit is discarded.

In other implementations, the battery can also be rechargeable where the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with cord that connects to the handheld unit. The circuitry in the handheld unit can include a recharger circuit (not shown). Batteries with rechargeable battery chemistry may be sometimes used as disposable batteries, where the batteries are not recharged but disposed of after use.

Use of Wavelengths for Optical Probing

Oxygenated and deoxygenated hemoglobin concentrations, from which oxygen saturation can be calculated, can be related to the absorption coefficient $\mu_a$ of a region of tissue for a given wavelength of light. In some cases, a simple relationship is used for calculation where the absorption coefficient is assumed to depend only on the concentrations of oxygenated and deoxygenated hemoglobin. However, melanin and water present in tissue can also absorb incident light so this simple relationship may be insufficient for highly accurate concentration calculations, as absorption from water and melanin may be incorrectly attributed to oxygenated or deoxygenated hemoglobin. A relationship between the absorption coefficient and the concentrations of oxygenated hemoglobin (HbO2), deoxygenated hemoglobin (Hb), water (H2O), and melanin (mel) may be:

$$\mu_a = 2.303(\varepsilon_{HbO2}[HbO2] + \varepsilon_{Hb}[Hb] + \varepsilon_{H2O}[H2O]\varepsilon_{mel}[mel])$$

where $\varepsilon_{species}$ denotes the molar absorptivity of a given species and bracketed quantities indicate concentration values.

The shape of a reflectance curve (generated by plotting the intensity of diffusely reflected or re-emitted light) can be analyzed to obtain the absorption and scattering coefficients for a given region of tissue. There are four unknown concentrations (i.e., [HbO2], [Hb], [H2O], and [mel]) in the above relationship that correspond to the absorption coefficient. Once the absorption coefficient is determined for a given wavelength, the relationship becomes an equation of four unknown variables. However, since the concentrations of oxygenated and deoxygenated hemoglobin, water, and melanin should not vary considerably over the course of a probe measurement, probing the tissue with four different wavelength emitted by the wavelength sources can provide four values for $\mu_a$, which can be used to determine the four relevant concentrations in the expression for $\mu_a$. That is, a system of four equations with four unknown variables can be solved, as is well understood. From the determined concentrations of oxygenated hemoglobins [HbO2] and deoxygenated hemoglobins [Hb], the oxygen saturation of tissue can be determined.

According to the embodiment where three wavelengths are emitted by the wavelength sources, the contributions from water, melanin, and other light absorbers can be combined into a single term and expressed as:

$$\mu_a = 2.303(\varepsilon_{HbO2}[HbO2] + \varepsilon_{Hb}[Hb] + \varepsilon_{H2O,mel}[H2O, mel]).$$

If three absorption coefficients $\mu_a$ are determined for the three wavelengths, then the three relevant concentrations for [HbO2], [Hb], and [H2O,mel]) can be determined, and the oxygen saturation can again be determined from the determined concentrations of oxygenated and deoxygenated hemoglobins. The absorption coefficients may be determined from the reflectance data by a variety of methods, such as fitting the reflectance data to one or more predetermined reflectance curves, where each predetermined reflectance curve represents a unique absorption coefficient. The absorption coefficients may alternatively be determined by vector multiplication with the net analyte signal, which is described in U.S. Pat. No. 6,597,931, titled "System and Method for Absolute Oxygen Saturation," and is incorporated by reference.

Wavelength Source Control

The wavelength sources may be cycled on and off at a variety of frequencies. For example, the wavelength sources may be turned on in sequence with one wavelength source on at any one time. The wavelength sources may be cycled at 30 hertz. Additionally each wavelength source may be modulated at a variety of frequencies in order to reject ambient light. For example, each wavelength source may be individually modulated at 2.5 kilohertz. Further, the wavelength sources may be individually cycled in a specific order. Detectors 125 may be substantially continuously monitored as the wavelength sources are cycled. Processor 505 may control the cycle order of the wavelength sources. Based on the cycle order, the reflectance data collected by detectors 125 may be appropriately categorized according to wavelength based on the known cycling of the wavelength sources on and off. The reflectance data may be stored in memory 510 for use by processor 505 in determining the oxygenated and deoxygenated hemoglobin concentrations and to further determine the oxygen saturation of tissue being probed.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
providing a sensor head for a tissue oximetry device comprising:
a plurality of detector structures arranged symmetrically in a symmetric arrangement, symmetric about a point on a line passing through a closed shape of the symmetric arrangement;
a first source structure at a first point of the closed shape of the symmetric arrangement, wherein the first source structure is configured to emit at least a first wavelength of light longer than about 730 nanometers;
a second source structure positioned at a second point of the closed shape of the symmetric arrangement, wherein the first and second source structure are positioned on a line on the sensor head, and the second source structure is configured to emit at least a second wavelength of light longer than about 730 nanometers;
a first detector structure on the closed shape of the detector structures, wherein a first distance is from the first detector structure to the first source structure, a second distance is from the first detector structure to the second source structure, and the first distance is greater than the second distance;
a second detector structure on the closed shape of the detector structures, wherein a third distance is from the second detector structure to the first source structure, a fourth distance is from the second detector structure to the second source structure, and the fourth distance is greater than the third distance;
a third detector structure on the closed shape of the detector structures, wherein a fifth distance is from the third detector structure to the first source structure, a sixth distance is from the third detector structure to the second source structure, the fifth distance is different from the first distance and the second distance, and the sixth distance is different from the first distance and the second distance; and
a fourth detector structure on the closed shape of the detector structures, wherein the first, second, third, and fourth detectors structures are not on the line, a seventh distance is from the fourth detector structure to the first source structure, an eighth distance is from the fourth detector structure to the second source structure, the seventh distance is different from the first, second, and fifth distances, and the eighth distance is different from the first, second, and sixth distances; and
determining an oxygen saturation value for a tissue to be measured using the first wavelength of light from the first source structure and the second wavelength of light from the second source structure emitted into the tissue and corresponding reflected light received by at least two of the detector structures.

2. The method of claim 1 wherein the determining an oxygen saturation value for a tissue comprises:
receiving digital reflectance data for the reflected light received by the at least two of the detector structures;
calculating absorption coefficients using the digital reflectance data;
solving a set of reflection coefficient equations for the tissue to be measured using the absorption coefficients to determining concentration values of at least oxygenated hemoglobin and deoxygenated hemoglobin; and
determining an oxygen saturation value for the tissue using the concentration values of oxygenated hemoglobin and deoxygenated hemoglobin.

3. The method of claim 1 wherein the first wavelength of light is at least one of 760 nanometers, 810 nanometers, 850 nanometers, or 900 nanometers.

4. The method of claim 1 wherein the first wavelength of light is at least one of 760 nanometers, 810 nanometers, or 850 nanometers, and the second wavelength of light is at least one of 760 nanometers, 810 nanometers, 850 nanometers, or 900 nanometers.

5. The method of claim 1 wherein the tissue oximetry device is a handheld tissue oximetry device comprising the housing comprising a processor, memory, display, and battery, and the sensor head is coupled to the housing.

6. The method of claim 1 wherein an enclosure of the tissue oximetry device comprises the sensor head, the sensor head is at an end of the tissue oximetry device, and when the sensor head is placed against the tissue to be measured, a display of the tissue oximetry device faces a user, and the display is coupled to the enclosure.

7. The method of claim 1 wherein the first and second source structures are coupled via waveguides to light emitting diodes.

8. The method of claim 1 wherein the first and second source structures are coupled via optical fibers to light emitting diodes.

9. The method of claim 1 wherein the first and second source structures comprise light emitting diodes.

10. The method of claim 1 wherein the first, second, third, and fourth detector structures are coupled via waveguides to photodetectors.

11. The method of claim 1 wherein the first, second, third, and fourth detector structures are coupled via optical fibers to photodetectors.

12. The method of claim 1 wherein the first, second, third, and fourth detector structures comprise photodetectors.

13. The method of claim 1 wherein the first and second source structures are coupled via optical fibers to light emitting diodes, and the first, second, third, and fourth detector structures comprise photodetectors.

14. The method of claim 1 wherein the first and second source structures are coupled via waveguides to light emitting diodes, and the first, second, third, and fourth detector structures comprise photodetectors.

15. The method of claim 1 wherein the closed shape is a circle.

16. The method of claim 1 wherein the first and second source structures are not between the first and second detector structures.

17. A method comprising:
providing a sensor head for a tissue oximetry device comprising:
a plurality of detector structures arranged symmetrically in a symmetric arrangement, symmetric about a point on a line passing through the symmetric arrangement;
a first source structure at a first point of the symmetric arrangement, wherein the first source structure is configured to emit at least a first wavelength of light longer than about 730 nanometers;
a second source structure positioned at a second point of the symmetric asymmetric arrangement, wherein the first and second source structure are positioned on a line on the sensor head, and the second source structure is configured to emit at least a second wavelength of light longer than about 730 nanometers;
a first detector structure of the detector structures, wherein a first distance is from the first detector structure to the first source structure, a second distance is from the first detector structure to the second source structure, and the first distance is greater than the second distance;
a second detector structure of the detector structures, wherein the first and second detector structures are not on the line, the first and second source structures are not between the first and second detector structures, a third distance is from the second detector structure to the first source structure, a fourth distance is from the second detector structure to the second source structure, and the fourth distance is greater than the third distance; and
determining an oxygen saturation value for a tissue to be measured using the first wavelength of light from the first source structure and the second wavelength of light from the second source structure emitted into the tissue and corresponding reflected light received by at least two of the detector structures.

18. The method of claim 17 comprising:
a third detector structure of the detector structures, wherein a fifth distance is from the third detector structure to the first source structure, a sixth distance is from the third detector structure to the second source structure, the fifth distance is different from the first distance and the second distance, and the sixth distance is different from the first distance and the second distance.

19. The method of claim 18 comprising:
a fourth detector structure of the detector structures, wherein a seventh distance is from the fourth detector structure to the first source structure, an eighth distance is from the fourth detector structure to the second source structure, the seventh distance is different from the first, second, and fifth distances, and the eighth distance is different from the first, second, and sixth distances.

20. The method of claim 17 wherein the determining an oxygen saturation value for a tissue comprises:
receiving digital reflectance data for the reflected light received by the at least two of the detector structures;
calculating absorption coefficients using the digital reflectance data;
solving a set of reflection coefficient equations for the tissue to be measured using the absorption coefficients to determining concentration values of at least oxygenated hemoglobin and deoxygenated hemoglobin; and
determining an oxygen saturation value for the tissue using the concentration values of oxygenated hemoglobin and deoxygenated hemoglobin.

21. The method of claim 17 wherein the symmetric arrangement is a circular arrangement.

* * * * *